United States Patent [19]

Berndt

[11] Patent Number: 5,038,938

[45] Date of Patent: Aug. 13, 1991

[54] DISPOSABLE SANITARY ARTHORCENTESIS RESERVOIR

[75] Inventor: Dieter R. Berndt, Allenwood, N.J.

[73] Assignee: DDJ Enterprises, Inc., Hauppauge, N.Y.

[21] Appl. No.: 545,631

[22] Filed: Jun. 28, 1990

[51] Int. Cl.⁵ .......................................... B65D 69/00
[52] U.S. Cl. .................................. 206/571; 206/570; 206/438; 206/365; 604/403; 604/411; 604/415; 604/416; 604/199
[58] Field of Search .............................. 206/570-572, 206/438, 364-366; 604/403, 406, 411, 414, 415, 416, 199

[56] References Cited

U.S. PATENT DOCUMENTS

| | | | |
|---|---|---|---|
| 4,261,474 | 4/1981 | Cohen | 215/250 |
| 4,265,242 | 5/1981 | Cohen | 128/272 |
| 4,362,241 | 12/1982 | Williams | 206/210 |
| 4,366,901 | 1/1983 | Short | 206/210 |
| 4,850,484 | 7/1989 | Denman | 206/366 |

FOREIGN PATENT DOCUMENTS 1000248  8/1965  United Kingdom ................ 206/438

Primary Examiner—Paul T. Sewell
Assistant Examiner—Thomas P. Hilliard
Attorney, Agent, or Firm—Mark T. Basseches; Paula T. Basseches

[57] ABSTRACT

A disposable tray assembly forming a housing for an aspiration kit is disclosed. The tray assembly includes a base and an upper tray member sealingly connected to the base to define a sealed internal chamber or reservoir for extracted fluids. Access to the reservoir is provided by an elastomeric plug through which a needle may be inserted. A soluble capsule filled with disinfectant is in registry with the plug so that fluids discharged by the needle are subjected to the disinfectant.

5 Claims, 2 Drawing Sheets

DISPOSABLE SANITARY ARTHORCENTESIS RESERVOIR

BACKGROUND OF THE INVENTION

1. Field of the invention

The present invention is in the field of aspirating devices and relates more specifically to a disposable tray which may be used as an element of a kit for aspirating synovial fluids or the like and as a reservoir for the aspirated fluids.

2. The Prior Art

It has been determined that synovial fluids are a medium for the growth of HIV virus strains. Prior to such determination it had been conventional practice to discharge fluids aspirated e.g. from the joint of a patient, into the waste lines of hospitals. Following such determination regulations have mandated that the fluids be disposed of in the manner of contaminated medical wastes.

In a typical aspirating procedure a number of components are required, including means for applying a local anesthetic, a topical disinfectant, a needle and syringe for drawing fluid, one or more specimen tubes for receiving test samples of the fluid, bandage means for covering the incision.

It has been proposed to package these components inter alia in a unitary kit.

With the advent of the necessity for sanitary disposition of the fluids the physician has been required to provide ancillary sealed disposal means. Also, the needle, which is likely to be contaminated in the event of the presence of HIV virus, must be separately and safely disposed of.

U.S. Pat. No. 4,085,845 of Apr. 25, 1987 discloses a kit including a utility tray for the storage of dental components and associated articles to be used during a dental procedure.

SUMMARY OF THE INVENTION

The present invention may be summarized as directed to a disposable sanitary tray device to be used as an element of an aspiration kit whereby the components necessary to effect the procedure may be stored in the kit. A characterizing feature of the invention resides in the tray component being of sealed double wall construction and forming a sealed reservoir or chamber for the reception of the drained fluids, the chamber including a self sealing entrance way whereby the aspirated fluids contained in a syringe may be injected into the chamber for sanitary disposal, the act of injecting the fluids in addition serving simultaneously to disinfect the fluids and the syringe needle.

Still more particularly, the invention is directed to a polymeric tray having a sealed interior chamber and defining on its upper surface means for storing the components of an aspirating kit, the interior of the tray being accessible solely through an elastomeric plug supporting a disinfectant capsule interiorly of the chamber. Fluids are discharged into the interior of the tray by insertion of a needle through the plug and into the capsule, whereby the fluids are disinfected, and function also to dissolve the soluble capsule at the same time functioning to disinfect the needle employed to discharge the fluids.

It is accordingly an object of the invention to provide a disposable tray adapted for use as an element of an aspirating kit, which tray functions as a receptacle for the kit elements, as a convenient means for holding specimen vials and as a sealed receptacle for the fluids aspirated.

Still a further object of the invention is the provision of a tray as described which functions automatically to disinfect the fluids discharged into the receptacle.

DETAILED DESCRIPTION OF THE DRAWINGS

Figure 1:
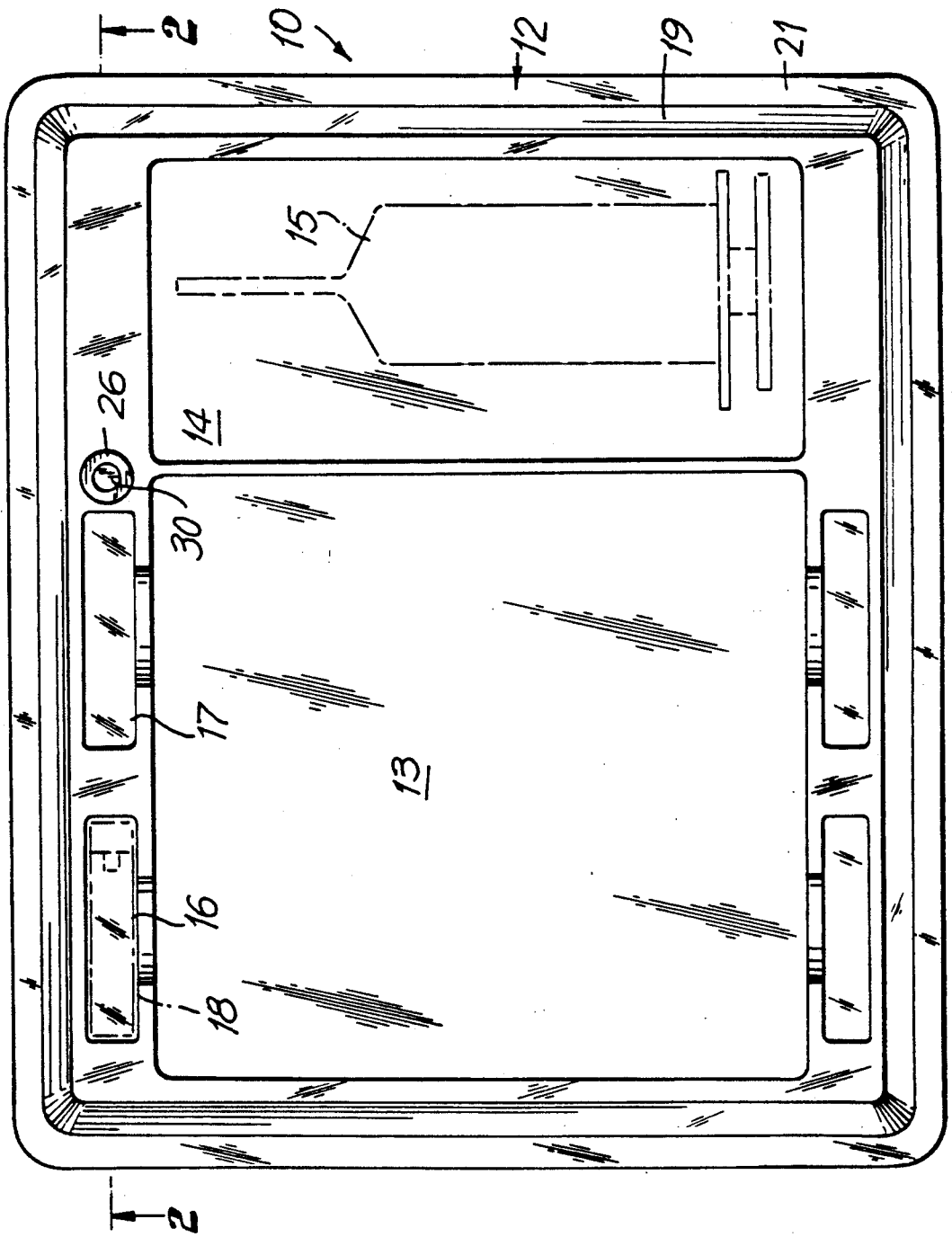
FIG. 1 is a top plan view of a reservoir device in accordance with the invention.
Figure 2:
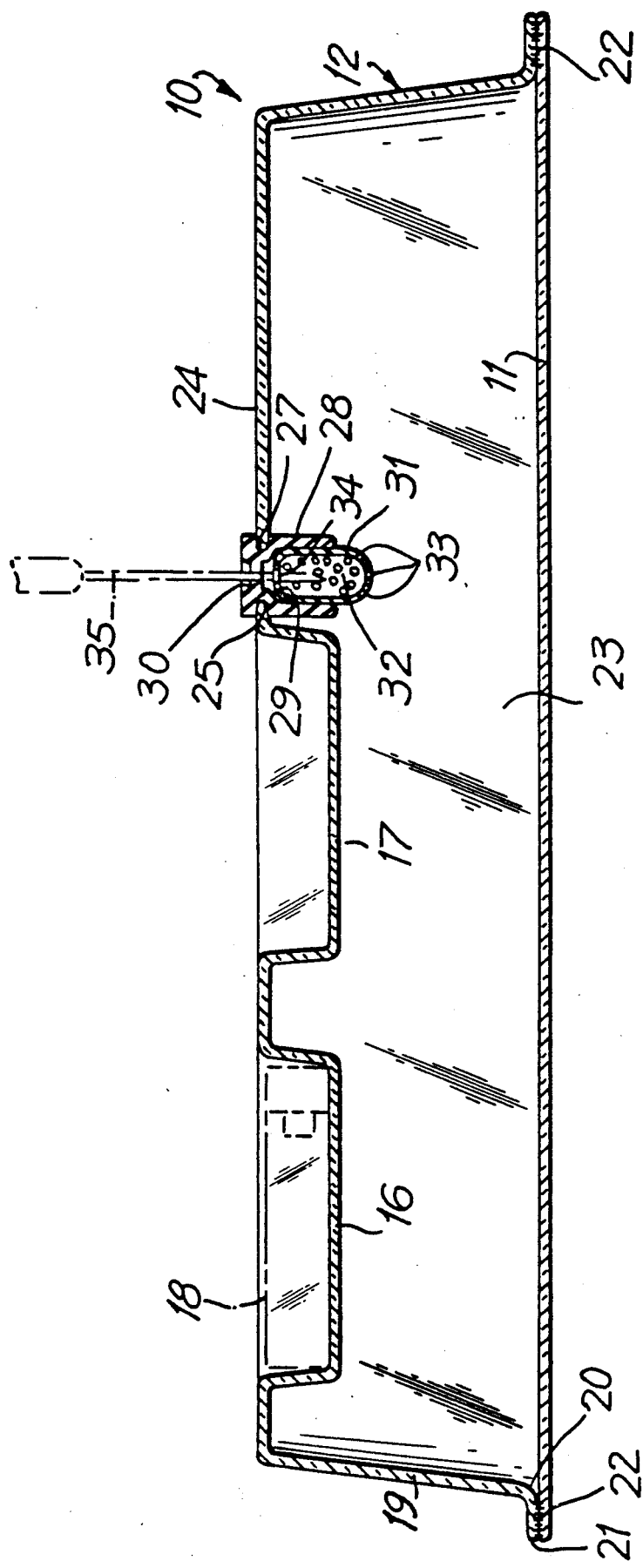
FIG. 2 is a vertical section taken on the line 2--2 of FIG. 1.

Referring now to the drawings, there is shown in FIG. 1 a disposable sanitary tray which desirably may be distributed as a kit. The tray assembly 10, which is preferably formed of a thin vacuum-formed transparent polymeric material, such as acetate, includes a planar base portion 11 and a tray member 12.

As best seen in FIG. 1, the tray member 12 may include a plurality of recesses 13,14 which function as compartments for receiving the operative elements of the kit, such as syringe 15, needles, sterile bandages, etc. Optionally, the tray 12 may include depressed portions, such as portions 16,17 for the accommodation of specimen vials 18.

The tray member 12 includes a depending continuous skirt or side wall 19, the lowermost edge 20 of which extends laterally outwardly to define integral planar marginal flange 21. The flange 21 is connected to base 11 about a continuous seal line 22 whereby there is defined between the tray member 12 and base 11 a sealed compartment 23.

There is formed, preferably in the upper wall 24 of the tray member 12, an aperture 25 extending to the interior of chamber 23. An elastomeric plug member 26 is sealingly mounted in the aperture 25, the plug member including an annular recess 27 within which the walls defining aperture 25 are located to support the plug in sealing condition of the aperture.

The plug 26 includes a depending tubular portion 28 disposed within chamber 23, the tubular portion incorporating a recess 29. A thin membrane portion 30 of the plug separates the recess 29 from the exterior of the tray.

A thin walled capsule 31, which is preferably formed of gelatin, is firmly, frictionally mounted in the recess 29 within tubular member 28. The capsule 31 is filled with a granular disinfectant composition, i.e. sodium hypochlorite 32. The capsule includes one or more minute apertures 33 adjacent the lower portion thereof and optionally but preferably an upwardly directed aperture 34 in registry with the thin membrane portion 30 of the plug.

Desirably the entire tray assembly 10 is sold as a unit with various instruments, containers, syringe, bandages, specimen vials etc. housed with the compartment 13, 14, 15, 17, etc.

An encompassing impervious sleeve (not shown) is desirably formed about the kit to retain the various components within the respective compartments and maintain sanitary conditions within the kit prior to use.

In use, the sleeve is removed and the procedure of drawing fluids through the use of a syringe and needle in known manner is effected.

When the syringe 15 has been filled with the aspirated fluids and the desired quantities of such fluids required for testing purposes have been introduced into the vials 18, the major quantity of fluid remaining in the syringe is introduced into compartment 23.

This is done by inserting the hypodermic needle 35 attached to the syringe 15 through the membrane 30 of plug 26 and into the interior of the capsule 31. At this point the plunger of the syringe is depressed to discharge the remaining fluids into the disinfectant composition and through the capsule apertures 33 into the interior of compartment 23. Where a sufficient quantity of fluids is discharged, the lower portion of the capsule will dissolve and the contents fall into the chamber 23 where they will mix with and disinfect the fluids retained in such compartment.

The mixture of fluids and disinfectant in the capsule will also disinfect the tip of the needle and desirably, after initial ejection of fluids, the plunger may be partially withdrawn, extracting into the interior of the needle and syringe a solution of the disinfectant composition.

When discharge of the fluids has been completed needle 35 and syringe are disposed of in the manner of medical waste, as is the entire tray assembly 10 which, at this juncture, forms a sealed reservoir permanently containing the now disinfected fluids.

From the foregoing it will be appreciated that there is provided in accordance with the present invention a tray assembly which functions initially as an element of a kit providing a convenient means for supplying as a unit the apparatus necessary to perform an aspiration procedure and wherein the components may be maintained in a sanitary condition and in their desired compartment in the upper surface of the tray by an encircling impervious sheet. After removal of the sheet, the double-walled tray functions as a sealed depository for the potentially infectious fluids withdrawn, the juxtaposition of the desired disinfecting capsule assuring that the fluids are disinfected so that in the unlikely event of the rupture of the container the fluids are rendered harmless As will be apparent to those skilled in the art and familiarized with the instant disclosure, numerous changes in details of construction may be made without departing from the spirit of the invention, which is to be broadly construed within the scope of the appended claims

Having thus described the invention and illustrated its use, what is claimed as new and is desired to be secured by Letters Patent is:

1. A disposable arthrocentesis reservoir device comprising, in combination, a generally planar bse portion, a tray member having a top portion in parallel spaced relation to said base portion and downwardly extending side walls directed toward said base portion a planar marginal flange extending from said side walls, said flange being in co-planar alignment with and sealingly bonded to a surface of said base portion whereby said tray member and base portion define therebetween a sealed chamber, an aperture formed in said tray member leading to said chamber, an elastomeric plug sealingly mounted in said aperture, said plug including a penetrable outer wall portion located externally of said tray, a capsule mounted within said chamber in alignment with said plug, said capsule including an orifice opening into said chamber, and a second orifice directed toward said outer wall portion of said plug, said capsule having a soluble disinfectant material enclosed therein.

2. A reservoir device in accordance with claim 1 wherein said capsule is made of a soluble material.

3. A device in accordance with claim 2 wherein said plug includes a tubular portion disposed within said chamber, and said capsule is mounted within said tubular portion of said plug.

4. A reservoir device in accordance with claim 3 wherein said capsule is frictionally retained within said tubular portion of said plug.

5. A reservoir device in accordance with claim 1 and including depressions formed in said top wall and extending toward said bse, said depressions being sized to receive specimen vials and the like.

* * * * *